United States Patent
Engelhardt et al.

(10) Patent No.: US 7,897,937 B2
(45) Date of Patent: Mar. 1, 2011

(54) METHOD OF FLUORESCENCE-MICROSCOPICALLY IMAGING A STRUCTURE IN A SAMPLE WITH HIGH THREE-DIMENSIONAL SPATIAL RESOLUTION

(75) Inventors: Johann Engelhardt, Bad Schönborn (DE); Marion Lang, Garching (DE); Stefan Hell, Göttingen (DE)

(73) Assignees: Deutsches Krebsforschungszentrum, Heidelberg (DE); Max-Planck-Gesellschaft zur Förderung der Wissenschaften e.V., München (DE)

( * ) Notice: Subject to any disclaimer, the term of this patent is extended or adjusted under 35 U.S.C. 154(b) by 157 days.

(21) Appl. No.: 12/413,665

(22) Filed: Mar. 30, 2009

(65) Prior Publication Data

US 2009/0242801 A1 Oct. 1, 2009

(30) Foreign Application Priority Data

Mar. 31, 2008 (EP) .................................. 08006232

(51) Int. Cl.
*G01N 21/64* (2006.01)
(52) U.S. Cl. .................................................. 250/459.1
(58) Field of Classification Search ............... 250/459.1
See application file for complete search history.

(56) References Cited

U.S. PATENT DOCUMENTS

| | | | |
|---|---|---|---|
| 6,184,535 B1 | 2/2001 | Kashima et al. | |
| 6,667,830 B1 * | 12/2003 | Iketaki et al. | ............ 359/368 |
| 7,064,824 B2 | 6/2006 | Hell | |
| 2004/0212799 A1 | 10/2004 | Hell | |
| 2007/0023686 A1 | 2/2007 | Wolleschensky et al. | |
| 2007/0206278 A1 | 9/2007 | Dyba et al. | |
| 2008/0032414 A1 | 2/2008 | Zhuang et al. | |

FOREIGN PATENT DOCUMENTS

WO  WO 2006/127692 A2  11/2006

OTHER PUBLICATIONS

Stefan W. Hell, "Toward fluorescence nanoscopy," 2003, Nature Biotechnology, vol. 21, No. 11, pp. 1347-1355.*
Dybe et al., "Ultrafast dynamics microscopy," 2000, Applied Physics Letters, vol. 77, No. 4, pp. 597-599.*

(Continued)

*Primary Examiner*—David P Porta
*Assistant Examiner*—Kiho Kim
(74) *Attorney, Agent, or Firm*—Thomas, Kayden, Horstemeyer & Risley, LLP (57) ABSTRACT

For imaging a structure in a sample with spatial resolution, the structure is labeled with a fluorophore which is transferable by an optical transfer signal out of a first into a second photochromic state. Via a common objective, the sample is subjected to both the focussed optical transfer signal and a focussed optical excitation signal only exciting a portion of the fluorophore being in its second photochromic state for fluorescence. The transfer and the excitation signal have a common centre of maximum intensity; and a decrease of intensity of the transfer signal with the distance to this common centre is substantially stronger than any decrease of the effective return rate of the fluorophore back into the first photochromic state. Fluorescence light emitted by the excited fluorophore is detected. Then, the common centre is shifted with regard to the sample; and the steps of subjecting and detecting are repeated.

20 Claims, 4 Drawing Sheets

OTHER PUBLICATIONS

Tinnefeld et al., "Optical switches: Key molecules for improved fluorescence imaging and tracking with high optical resolution," 2007, SPIE Proceedings, vol. 6633, pp. 663303-1 to 663303-10.*

Matthias Nagorni and Stefan W. Hell "Coherent use of opposing lenses for axial resolution increase in fluorescent microscopy. I. Comparative Study of concepts" in J. Opt. Soc. Am. A/vol. 18, No. 1/Jan. 2001, p. 36-48.

Stiel, A. C., S. Trowitzsch, G. Weber, M. Andresen, C. Eggeling, S. W. Hell, S. Jakobs, and M. C. Wahl, "1,8A° bright-state structure of the reversibly switchable fluorescent protein Dronpa guides the generation of fast switching variants". Biochem. J. (2007) 402:35-42.

R. Ando, C. Flors, H. Mizuno, J. Hofkens and A. Miyawaki, "Highlighted Generation of Fluorescence Signals Using Simultaneous Two-Color Irradiation on Dronpa Mutants", Biophysical Journal: Biophysical Letters (2007), L97ff, DOI: 10.1529/biophysj.107. 105882.

Jonas Fölling, Vladimir Belov, D. Riedel, Andreas Schönle, Alexander Egner, Christian Eggeling, Mariano Bossi, and Stefan W. Hell, "Fluorescence Nanoscopy with Optical Sectioning by Two-Photon Induced Molecular Switching using Continuous-Wave Lasers", ChemPhysChem (2008), 9, 321-326, DOI: 10.1002/cphc. 200700655.

Betzig, E., G. Patterson, R. Sougrat, O. Lindwasser, S. Olenych, J. Bonifacino, M. Davidson, J. Lippincott-Schwartz, and H. Hess, "Imaging intracellular fluorescent proteins at nanometer resolution.", Science (2006), 313:1642-1645.

* cited by examiner

METHOD OF FLUORESCENCE-MICROSCOPICALLY IMAGING A STRUCTURE IN A SAMPLE WITH HIGH THREE-DIMENSIONAL SPATIAL RESOLUTION

CROSS REFERENCE TO RELATED APPLICATIONS

This application claims priority to co-pending European Patent Application No. EP 08 006 232.6 entitled "Method of fluorescence-microscopically imaging a structure in a sample with high three-dimensional spatial resolution", filed Mar. 31, 2008.

FIELD OF THE INVENTION

The invention relates to a method of fluorescence-microscopically imaging a structure in a sample with three-dimensional spatial resolution. Particularly, the invention relates to a method of imaging a structure in a sample comprising the steps of labelling the structure with a fluorophore; subjecting the sample in a spatially limited excitation-volume to an optical excitation signal exciting a portion of the fluorophore located in the excitation-volume for fluorescence; detecting fluorescence light emitted by the excited fluorophore located in and about a centre of maximum intensity of the excitation signal; shifting the centre of maximum intensity of the excitation signal with regard to the sample; and repeating the preceding steps of subjecting and detecting for the shifted centre of maximum intensity of the excitation signal.

BACKGROUND OF THE INVENTION

The resolution in a fluorescence microscope is given by the point spread function (PSF). In wide field microscope laterally extended structures are axially not resolved because of the missing cone in the optical transfer function (OTF). Further more out of focus structures blur the image of structures in the focus.

In 2-photon fluorescence microscopy, the fluorescence of the fluorophore in the sample is only excited by two photons of the optical excitation signal each providing a half of the necessary excitation energy. As a result, the PSF of the excitation of the fluorophore is depending on the square of the intensity distribution or of the PSF of the optical excitation signal. As compared to the PSF of the optical excitation signal, the square of the PSF of the optical excitation signal is more concentrated towards the centre of the excitation-volume in all directions, particularly including the axial direction in which the optical excitation signal is focussed into the sample. In this way the spatial resolution in axial direction is directly increased by 2-photon excitation of the fluorophore.

A further known measure to increase the axial resolution in fluorescence microscopy is confocal detection of the fluorescence light which means a spatial limitation of the detection volume out of which the fluorescence light is actually detected. Here, the effective PSF is the product of the PSF of the optical excitation signal and of the PSF of the detection arrangement. 2-photon excitation may also be combined with confocal detection.

In more elaborate approaches, the PSF of the optical excitation signal is spatially confined by means of superimposing coherent parts of the optical excitation signal for forming an interference pattern, the fluorophore substantially only being excited at the maxima of the interference pattern. A prominent type of this kind of fluorescence microscopy is 4Pi microscopy in which spherical wave fronts of the excitation signal are superimposed from two opposite directions in a common focal spot for forming an interference pattern. Within the focal spot, however, not only the first order maximum of the interference pattern is found at the centre but second order maxima flank this first order maximum on both sides of the focal plane. To make use of the full potential of 4Pi microscopy, the second order maxima have to be suppressed in some way. One option is 2-photon excitation as discussed above. Another option is coherent detection of the fluorescence light both providing a further factor of the total PSF.

A further approach of suppressing the fluorescence light from the second order maxima in 4Pi microscopy is forcing the fluorophore within the area of the second order maxima to stimulated emission of fluorescence light which is discriminated from the detected fluorescence light from the sample. Generally, in stimulated emission depletion (STED) fluorescence microscopy an excitation-volume in which fluorophore molecules have been excited for fluorescence is confined or reduced in dimensions by de-exciting a part of the fluorophore molecules within the excitation-volume, only leaving the fluorophore molecules within a strongly confined centre of the excitation-volume in their fluorescent state so that the registered fluorescence light can be assigned to the fluorophore molecules within a very small effective excitation-volume.

For a survey of the above methods of fluorescence microscopy see Matthias Nagorni and Stefan W. Hell "Coherent use of opposing lenses for axial resolution increase in fluorescent microscopy. I. Comparative Study of concepts" in *J. Opt. Soc. Am. A*/Vol. 18, No. 1/January 2001, p. 36-48.

The basic principle known from STED fluorescence microscopy is also applied in reversible saturable optical fluorescence transition (RESOLFT) microscopy in which photochromic fluorophores are used to confine the effective excitation-volume in which an optical excitation signal excites a fluorophore for fluorescence. To this end, a switching signal by which the photochromic fluorophore can be switched in an off or dark state and which has a zero point at the centre of the excitation-volume is also applied to the sample. If the zero point is a zero point of an interference pattern, and if the intensity of the switching signal is sufficiently high, the dimensions of the effective excitation-volume in which the fluorophore is still in its on or fluorescent state and from which the detected fluorescence light can exclusively origin may be kept far below the diffraction barrier (see, for example, U.S. Pat. No. 7,064,824).

The concept of switchable photochromic fluorophores is also used in photo-activated localization microscopy (PALM) (see WO 2006/127692 A2) and stochastic optical reconstruction microscopy (STORM). Here, such a small proportion of a total concentration of a photochromic fluorophore is switched on into its fluorescent state that the fluorescence light from the single fluorescent fluorophore molecules can be registered separately, and Gaussians are fitted to the PSF of the spatial distribution of the registered fluorescence light to determine the actual location of the fluorescent molecule with sub diffraction spatial resolution. When the few switched on fluorophore molecules photobleach, another subset of the fluorophore molecules is switched into the on state and the procedure is thus repeated for sufficient stochastically selected subsets of the fluorophore molecules to image a structure labelled with the fluorophore.

A strong disadvantage of PALM and STORM is the time consumed by the procedure which limits the observation of living samples, i.e. of objects in which the structure of interest changes with time, and the production of images which may be directly viewed with the human eye.

RESOLFT and STED microscopy as well as 4Pi microscopy and other similar approaches to high spatial three-dimensional resolution fluorescence microscopy also require sophisticated equipment.

2-Photon excitation of fluorophores leads to a 3-dimensional resolution without additional means but the fluorescence yield is comparably low. Additionally a large difference in the wavelengths of the excitation light and the fluorescence light has to be coped with in 2-photon fluorescence microscopy. In confocal laser scanners chromatic aberrations may also be limiting for the precision of the object registration. Here often some axial resolution has to be sacrificed to achieve a large enough signal strength by opening the detection pinhole which additionally requires precise optical alignment.

Ando et al. (2007, see "References") disclose a method of imaging a structure in a sample labelled with the photochromic fluorophore Dronpa. Via a common objective the sample is subjected to irradiation in a common focal spot both at 405 nm and at 488 nm, and fluorescence light emitted by the fluorophore is confocally detected. The irradiation at 405 nm transfers Dronpa out of a dark or non-fluorescent state into a fluorescence state. The irradiation at 488 nm excites Dronpa for emission of fluorescence light, and returns it into its dark or non-fluorescence state. Whereas the irradiation at either 405 nm or 488 nm alone produces no fluorescence light signal, the simultaneous irradiation at both wavelengths produces a fluorescence light signal. Confocal detection of this fluorescence light results in a spatial resolution typical for fluorescence microscopy with confocal detection. Ando et al. propose that it should be possible to spatially restrict the generated fluorescence signal, which can be collected in wide-field detection mode, if the two lasers supplying the irradiation light of the two different wavelengths are aligned independently using separate objectives.

A method of fluorescence microscopically imaging a structure in a sample with high 3-dimensional spatial resolution which provides additional spatial resolution as compared to known methods at little additional efforts would be highly appreciated.

SUMMARY OF THE INVENTION

In one aspect the invention provides a method of imaging a structure in a sample with three-dimensional spatial resolution, the method comprising the steps of: selecting a fluorophore from a group of photochromic fluorophores which are repeatedly temporarily transferable by means of an optical transfer signal out of a first photochromic state into a second photochromic state having fluorescence properties specific to the second photochromic state, and which display a return rate out of the second photochromic state into the first photochromic state; labelling the structure with the fluorophore; via a common objective, subjecting the sample in a spatially limited transfer-volume to the optical transfer signal transferring a portion of the fluorophore located in the transfer-volume into its second photochromic state; via the common objective, subjecting the sample in a spatially limited excitation-volume to an optical excitation signal exciting a portion of the fluorophore located in the excitation-volume and being in its second photochromic state for fluorescence, the transfer-volume and the excitation-volume having a common centre of maximum intensity of the transfer signal and of the excitation signal; wherein, at least in the direction of the optical axis of the common objective, a decrease of intensity of the transfer signal with the distance to the common centre of maximum intensity is substantially stronger than any decrease of the effective return rate of the fluorophore; detecting fluorescence light emitted by the excited fluorophore in its second photochromic state located in and about the common centre of maximum intensity of the transfer signal and the excitation signal; shifting the common centre of maximum intensity of the transfer signal and the excitation signal with regard to the sample; and repeating the preceding steps of subjecting and detecting for the shifted common centre of maximum intensity of the transfer signal and the excitation signal.

In a more detailed aspect the invention provides a method of imaging a structure in a sample with three-dimensional spatial resolution, the method comprising the steps of: selecting a fluorophore from a group of photochromic fluorophores which are repeatedly temporarily transferred out of a first photochromic state into a second photochromic state by means of an optical transfer signal by a process selected from a group of processes including: cis-/trans-isomerisation, proton transfer, atom group transfer, electron transfer, ring-opening/closing, and dimerisation, which are at least fluorescent in their second photochromic state and have fluorescence properties specific to the second photochromic state, and which display a return rate out of the second photochromic state into the first photochromic state, the return rate being inducible by means of a physical return signal; labelling the structure with the fluorophore; via a common objective, subjecting the sample in a spatially limited transfer-volume to the optical transfer signal transferring a portion of the fluorophore located in the transfer-volume into its second photochromic state; via the common objective, subjecting the sample in a spatially limited excitation-volume to an optical excitation signal exciting a portion of the fluorophore located in the excitation-volume and being in its second photochromic state for fluorescence, the transfer-volume and the excitation-volume having a common centre of maximum intensity of the transfer signal and of the excitation signal; via the common objective, subjecting the sample to the return signal, the intensity of the return signal having no minimum at the common centre of maximum intensity of the transfer signal and the excitation signal; wherein, at least in the direction of the optical axis of the common objective, a decrease of intensity of the transfer signal with the distance to the common centre of maximum intensity is substantially stronger than any decrease of the effective return rate of the fluorophore; detecting fluorescence light emitted by the excited fluorophore in its second photochromic state located in and about the common centre of maximum intensity of the transfer signal and the excitation signal; shifting the common centre of maximum intensity of the transfer signal and the excitation signal with regard to the sample; and repeating the preceding steps of subjecting and detecting for the shifted common centre of maximum intensity of the transfer signal and the excitation signal for three-dimensionally scanning the sample with the common centre of maximum intensity of the transfer signal and the excitation signal.

The new method comprises the steps of selecting a fluorophore from a group of photochromic fluorophores which are repeatedly temporarily transferable by means of an optical transfer signal out of a first into a second photochromic state having specific fluorescence properties, and which display a spontaneous and/or inducible return rate out of the second photochromic state into the first photochromic state; labelling the structure with the fluorophore; via a common objective, subjecting the sample both to the optical transfer signal in a spatially limited transfer-volume, and to an optical excitation signal exciting a portion of the fluorophore being in its second photochromic state for fluorescence in a spatially limited excitation-volume, the transfer-volume and the excitation-volume having a common centre of maximum intensity of the transfer signal and of the excitation signal, wherein, at least in the direction of the optical axis of the common objective, a decrease of intensity of the transfer signal with the distance to the common centre of maximum intensity is substantially stronger than any decrease of the effective return rate of the fluorophore; detecting fluorescence light emitted by the excited fluorophore; shifting the common centre of maximum intensity with regard to the sample; and repeating the preceding steps of subjecting and detecting.

The requirement that the intensity of the transfer signal decreases stronger with the distance to the common centre of maximum intensity than the effective return rate of the fluorophore in the direction of the optical axis of the common objective, is a precondition for increasing the spatial resolution in the direction of the optical or z-axis as desired with focussing both the transfer signal and the excitation signal via a common objective. This precondition is not met by Ando et al. Thus, they did not achieve any increase in spatial resolution over standard confocal detection in their actual setup.

Of course, there are further benefits of the new method, if the intensity of the transfer signal does not only decrease stronger with the distance to the common centre of maximum intensity than the effective return rate of the fluorophore in the direction of the optical axis of the common objective but also laterally thereto, i.e. within the focal plane of the common objective.

In the new method, the photochromic fluorophore is transferred into its second photochromic state or switched-on in a transfer-volume having a centre of maximum intensity of the transfer signal coinciding with the centre of maximum intensity of the excitation signal. I.e. the transfer signal and the excitation signal are spatially confined or localized to a common centre of maximum intensity. The detected fluorescence light is only emitted by the fluorophore which is both in its second photochromic state, i.e. switched on by means of the transfer signal, and excited by means of the excitation signal. Thus, in case of a dominant spontaneous off-rate or any other case in which the effective return rate of the fluorophore displays little dependency on the distance to the common centre of maximum intensity, the PSF of the emitted fluorescence light is both depending on the PSF of the transfer signal and the PSF of the excitation signal, i.e. a product of these two PSFs. In this way, an increase of the three-dimensional spatial resolution is obtained in addition to any other measures taken for increasing the spatial resolution in that a photochromic fluorophore is used as the fluorophore for labelling the structure of interest.

The new method may be combined with any further measures for increasing the spatial resolution. As such, the measure of increasing the spatial resolution of the method of the present invention does not decrease the yield of fluorescence light from the sample as known from 2-photon-excitation; and it can be executed without additional equipment as it will be seen from the following description. With suitably selected photochromic fluorophores, it is sufficient to use these fluorophores for labelling the structure of interest in the sample.

Generally, the group of photochromic fluorophores which may be used in the new method includes photochromic fluorophores which are at least fluorescent in their second photochromic state. They may also be fluorescent in their first photochromic state. In this case, however, there must be some way to discriminate or distinguish the fluorescent light emitted by the fluorophore in its first photochromic state from the fluorescence light emitted by the fluorophore in its second photochromic state. Such a discrimination may, for example, be effected by wavelength selection of the detected fluorescence light (with different emission spectra) or wavelength selection of the optical excitation signal (with different absorption spectra) or appropriate timing of the fluorescence light detection depending on the excitation (with different lifetimes of the excited fluorescent state).

More particular, the photochromic fluorophores which may be used in the new method are transferred between their first and second photochromic states by cis-/trans-isomerisation, proton transfer, atom group transfer, electron transfer, ring-opening/closing, dimerisation or such. Any inducible change which changes the spectral properties may be used. Those skilled in the art will be aware of various photochromic fluorophores which fulfil these requirements. One group of such photochromic fluorophores is made up by photochromic proteins including mutants of the green fluorescent protein (GFP) like for example DRONPA, Fastlime, switchable Rhodamine derivates etc. Photochromic proteins are particularly suitable as photochromic fluorophores in the new method as they may be expressed by biological samples as a part of the structure of interest in the sample. In this way, no later "staining" of the already existing structure of interest in the sample is necessary.

Within the groups defined above, the fluorophore may be selected from a group of fluorophores which display a substantial spontaneous return rate at ambient temperature of the sample. Even if this condition is met, the lifetime of the fluorophore in its second photochromic state will be comparatively long so that its effective excitation cross-section for excitation by the excitation signal is comparatively large. The lifetime of the second photochromic state of the fluorophore, however, does in no way limit the measuring time in the new method, as the transfer signal may continuously be applied to the sample so that any return rate of the fluorophore out of its second photochromic state into its first photochromic state is compensated for. The ambient temperature of the sample is that temperature at which the relevant steps of the new method are executed. It may be a reduced or even an increased temperature with regard to room temperature.

The fluorophore may alternatively or additionally be selected from a from a group of fluorophores which display a substantial return rate inducible by means of a return signal. The return signal may be used after detection of the fluorescence light to completely reset the fluorophore prior to measure the sample at another point of interest defined by the common centre of maximum intensity of the transfer signal and the excitation signal. It may, however, also be used simultaneously with the transfer signal to adjust a suitable proportion of the fluorophore consisting of a varying subset of the fluorophore molecules being in its second state at any relevant point in time. The return signal may be an electric, a magnetic, or any other physical signal. Preferably, however, it is an optical signal like the transfer signal and the excitation signal. In contrast to the transfer signal and the excitation signal, however, the return signal does not have to be a localized signal, and it should not be as localized as the transfer signal as this would be counterproductive in view of the desired distribution of the effective return rate. Thus, the sample should be subjected to the return signal in a larger area than the transfer-volume or even everywhere.

Conveniently, the sample is subjected to the optical return signal via the common objective used for the transfer signal and the excitation signal. In contrast to RESOLFT-techniques, however, the intensity of the return signal will have no zero point, preferably no minimum, but most preferably even a maximum at the common centre of maximum intensity of the transfer signal and the excitation signal. A maximum of the return signal at the common centre of maximum intensity is for example achieved, if the sample is subjected to a uniform intensity distribution of the return signal about the common centre of maximum intensity, as there will be no higher intensity of the return signal than in the common centre of maximum intensity.

Independent on how the fluorophore returns into its first photochromic state, it must be possible to repeatedly temporarily transfer it out of its first state into its second state to make benefit of the increase in three-dimensional spatial resolution in the method of the present invention. The possibility of repeatedly temporally transferring the fluorophore out its first photochromic state into its second photochromic state is a precondition of measuring the sample in closely adjacent points of interest.

In the new method the excitation-volume may be structured or spatially limited, for example, in that it is defined by a local constructive interference of a plurality of different parts of the excitation signal. Typically, two parts of the excitation signal are superimposed. The excitation-volume may, however, also be defined by simply focussing the excitation signal from one side into the sample, i.e. by the dimensions of a simple focal spot, or structured into any single or multi spot, single or multi line, or any other lateral or spatial pattern by any means, including projection means.

In the new method, the transfer-volume may also be defined by a local constructive interference of a plurality of different parts of the transfer signal. As the centres of maximum intensity of both the excitation-volume and the transfer-volume coincide in the new method, the excitation signal and the transfer signal may generally be directed onto the sample in the same way. For example, the excitation signal and the transfer signal may be both split up in two parts which are superimposed in the transfer-volume and the excitation-volume out of opposite directions through two lenses arranged on opposite sides of the sample. In this arrangement the beam paths of the different parts of both the excitation signal and the transfer signal should differ by less than the coherence length of the excitation signal and the transfer signal to enable the formation of the desired interference pattern with the constructive interference of both the excitation signal and the transfer signal in the common centre of the excitation-volume and the transfer-volume located about the coinciding focal points of the two lenses. This arrangement corresponds to 4Pi-fluorescence microscopy if the aperture angles of the two lenses are sufficiently large.

The new method may not only be combined with the known 4Pi-fluorescence microscopy. A combination with other methods of fluorescence microscopy, in which both a PSF of the excitation of the fluorophore and the PSF of the registration of the fluorescent light from the fluorophore are relevant, is also possible. Thus, the excitation signal may excite the fluorophore via a multi-photon process for fluorescence, like for example in 2-photon excitation, and/or the optical transfer signal may transfer the fluorophore into its second photochromic state via a multi-photon process.

Preferably, the new method is combined with confocal detection of the fluorescence light emitted by the fluorophore both being in its second photochromic state and excited by the excitation signal. Thus, the fluorescence light may be detected in a spatially limited detection-area having a centre which is confocally arranged with regard to the common centre of maximum intensity of the transfer signal and the excitation signal.

The high three-dimensional spatial resolution of the new method due to the multiplication of the PSF of the excitation signal by the PSF of the transfer signal may not only be used in three-dimensionally scanning a sample, although this application of the new method is a preferred embodiment. The high three-dimensional spatial resolution of the method of the present invention is a substantial advantage, even if the sample is only scanned in one or two dimensions. For three-dimensionally scanning the sample, the common centre of maximum intensity of the transfer signal and the excitation signal is shifted with regard to the sample in three linearly independent directions to completely cover at least one area of the sample extending in all three dimensions.

In the new method, both the transfer signal and the excitation signal are limited to a spatially limited volume. The benefits resulting from the effective PSF of the excitation of the fluorophore in the new method being a product of the PSF of the transfer signal and the PSF of the excitation signal, however, are only maximum in a spatial direction of interest, if the transfer signal and the excitation signal have essentially a same width at half maximum in that direction about the common centre of maximum intensity of the transfer signal and the excitation signal. Otherwise, the product of both individual PSFs is not significantly localized over the already more localized individual PSF.

In addition, a maximum benefit is only obtained from the new method, if the transfer signal and the excitation signal are both below a saturation intensity above which the proportion of the fluorophore transferred into its second photochromic state or excited for fluorescence is no longer linearly correlated to the intensity of the transfer signal or the excitation signal. In general, saturation should be avoided in all transitions involved, as it would potentially reduce the spatial resolution.

The new method is not depending on any of the optical signals used being pulsed signals. Instead, all optical signals to which the sample is subjected may be continuous wave signals. However, the use of pulsed optical signals is also possible.

Particularly, the return signal may be a pulsed signal completely returning the fluorophore into the first photochromic state prior to the steps of subjecting the sample to the transfer signal and the excitation signal and of detecting fluorescence light. This strong return signal strongly contributes to the relevant time-averaged spatial distribution of the effective return rate of the fluorophore. In fact, it ensures that the effective return rate of the fluorophore decreases less with the distance to the common centre of maximum intensity of the transfer signal and the excitation signal than the intensity of the transfer signal as required in the new method, even if the excitation signal, for example, induces a localized contribution to the effective return rate which as strongly decreases with the distance to the common centre of maximum intensity as the intensity of the transfer signal.

The absorption spectra of known photochromic fluorophores suitable for use in the present invention often display an absorption peak for the excitation signal that shows overlapping with an absorption peak for the transfer signal or for a return signal. Thus, the transfer signal and the excitation signal or the return signal and the excitation signal may be identical, if they have a wavelength within one of these overlaps. With identical transfer and excitation signals, for example, the execution of the new method is particularly simple in that it only requires the selection of an appropriate photochromic fluorophore to achieve the additionally three-dimensionally limited effective PSF of the excitation of the fluorophore for fluorescence. As a result, a standard fluorescence microscope, particularly a fluorescence microscope with confocal detection of the fluorescence light emitted from a sample may be easily upgraded for three-dimensionally imaging a sample in that a mechanism is provided which allows for additionally axially shifting the focal spot of one beam of light both providing the transfer signal and the excitation signal within the sample.

Other features and advantages of the present invention will become apparent to one with skill in the art upon examination of the following drawings and the detailed description. It is intended that all such additional features and advantages be included herein within the scope of the present invention, as defined by the claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views.

BRIEF DESCRIPTION OF THE DRAWINGS

In the following, the invention is further explained and described with respect to preferred exemplary embodiments illustrated in the drawings.

DETAILED DESCRIPTION

Figure 1:
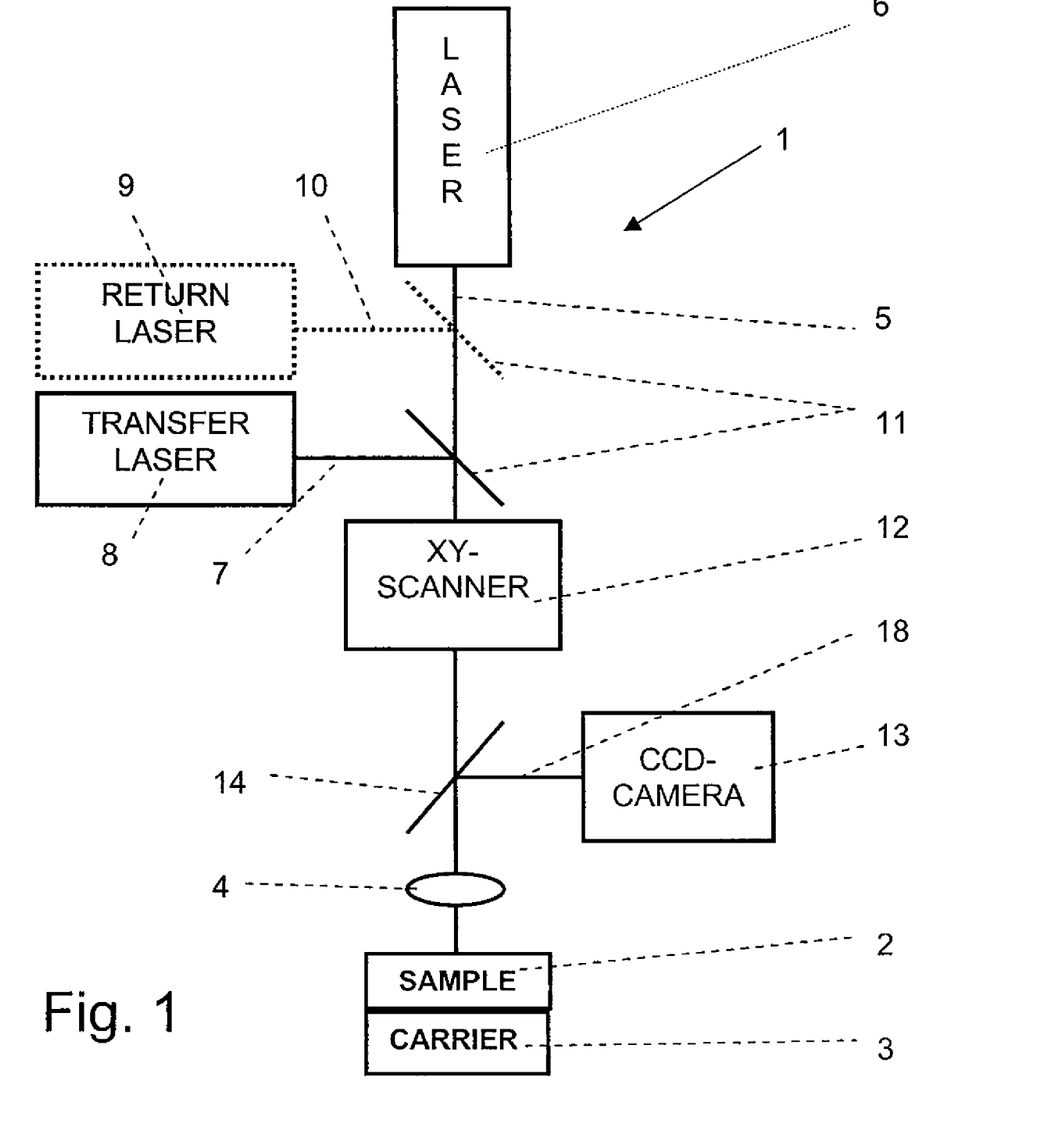
FIG. 1 is a schematic drawing of a fluorescence microscope useable for executing the new method of fluorescence-microscopically imaging a structure in a sample with three-dimensional spatial resolution.

Referring now in greater detail to the drawings, the fluorescence microscope 1 depicted in FIG. 1 is used for three-dimensionally imaging a structure in a sample 2. The sample 2 is arranged on a sample carrier 3 suitable for displacing the sample 2 in the axial direction of an objective 4. The objective 4 is used for focussing both an optical excitation signal 5 coming from an excitation laser 6 and an optical transfer signal 7 coming from a transfer laser 8 into a common focal spot within the sample 2. As the excitation signal 5 and the transfer signal 7 may have the same wavelength in the method of the present invention, the additional transfer laser 8 is optional. Further, a return laser 9 supplying an optional return signal 10 which is focussed in the pupil of the objective 4 may be provided. Dichroitic mirrors 11 are used to combine any optical signals 5, 7, and 10 onto one common optical axis. A xy-scanner laterally shifts the common optical axis of the optical signals 5, 7, and 10 to scan the sample 2 with the common focal spot of these optical signals within the focal plane of the objective 4. The third dimension for three-dimensionally scanning the sample 2 is provided by the sample carrier 3. In the common focal spot of the optical signals 5 and 7 a fluorophore in the sample 2 is excited for fluorescence. The fluorescence light 18 spontaneously emitted by the fluorophore in the sample 2 is detected via the objective 4 by a CCD-camera 13, a dichroitic mirror 14 reflecting the fluorescence light away from the optical signals 5 and 7. The CCD-camera 13 may be used to simulate a confocal detection of the fluorescence light 18 emitted out of the focal spot in the sample 2, or a confocal pinhole (not depicted here) may be provided to this end. The fluorophore may not only be stimulated for fluorescence in one common focal spot or line having a common centre of maximum intensity of the optical signals 5 and 7 but in a plurality of such common spots or lines sufficiently separated for separately registering the fluorescence light emitted out of these spots with the CCD-camera 13.

Figure 2:
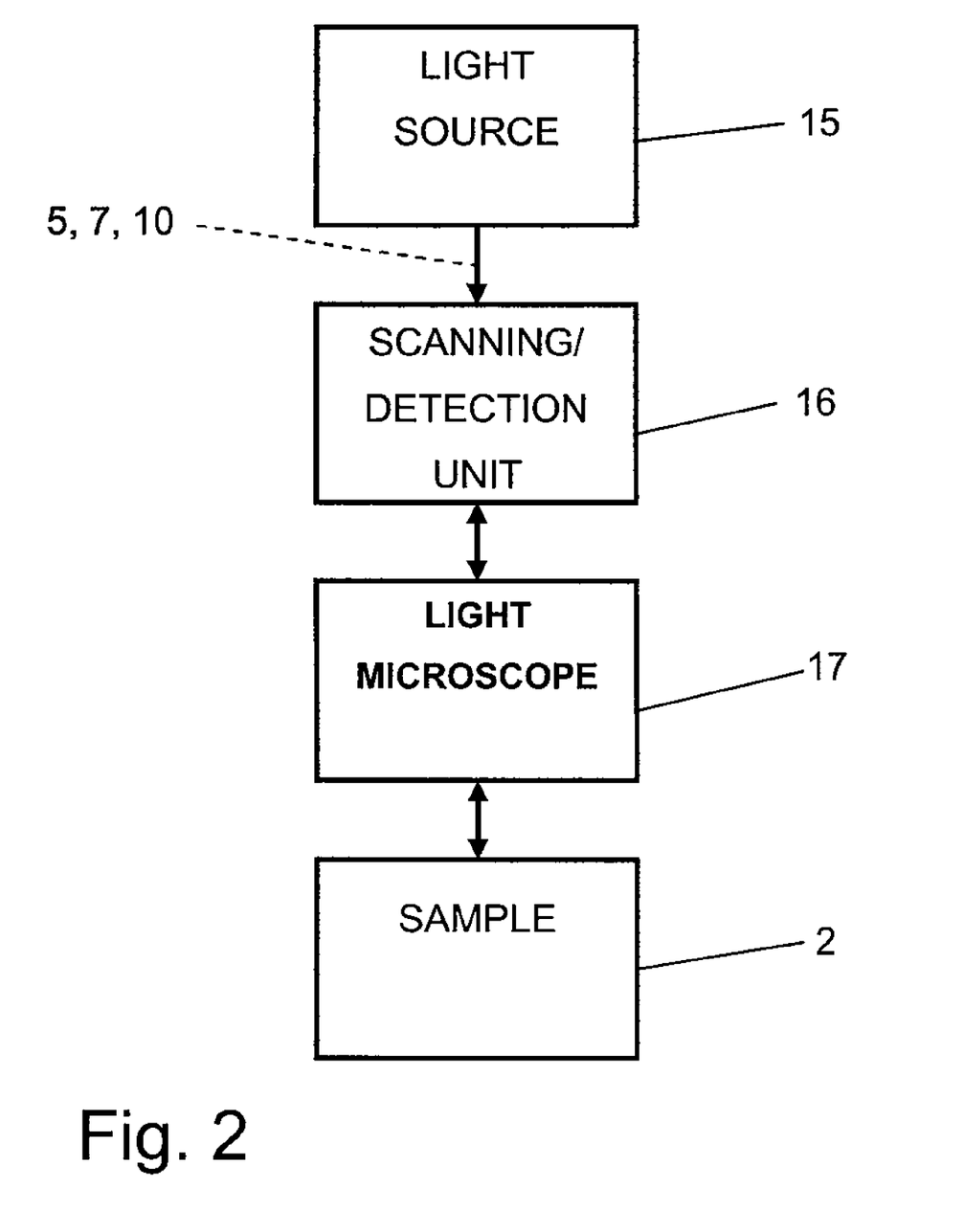
FIG. 2 is a block diagram generally indicating the functional units used for carrying out the new method.

The block diagram of FIG. 2 refers to the basic functional units required for executing the new method like, for example, with the fluorescence microscope 1 according to FIG. 1. A light source 15 provides the optical signals 5, 7, and 10, if required. The light source 15 may include the lasers 6, 8 and 9 according to FIG. 1. These lasers may be pulsed lasers or continuous wave lasers. The lasers may be single line lasers. Instead of two different lasers a multiline laser may be used, or even only one line of a multiline laser may be selected. Further, a white light laser may also be suitable. Instead of lasers the light source 15 may comprise LEDs, bulbs, MP-lasers or any other light sources with appropriate wavelengths and powers of the emitted light, which are required for transferring, exciting and/or returning the fluorophore in the sample 2. The optical signals 5, 7, 10 are supplied by the light source 15 to a structuring/scanning and detection unit 16. This unit 16 may form single or multiple spots or lines or any focusable structure out of the optical signals 5 and 7, while it more uniformly distributes the return signal 10, and shifts the spatial position of all these signals 5, 7, and 10 to scan the sample 2. Further, the unit 16 confocally detects the fluorescence light emitted by the sample 2. Thus, the unit 16 includes the xy-scanner 12, the sample carrier 3, the dichroitic mirror 14 and the CCD-camera 13 according to FIG. 1. A light microscope 17 is provided to project the structure formed by the unit 16 into the sample 2 and to provide the fluorescence light from the sample 2. This light microscope may be a widefield microscope, a 4PI-microscope or any other suitable light microscope. The objective 4 according to FIG. 1 is part of the light microscope 17.

The three-dimensional optical resolution in imaging a structure in the sample 2 labelled with a fluorophore essentially is the product of an excitation PSF (point spread function) defining an effective excitation-volume in which the fluorophore is excited for fluorescence multiplied by a detection PSF defining the detection-volume out of which fluorescence light emitted by the fluorophore in the sample 2 is detected The detection PSF depends on the setup of the light microscope 17 and of the detection part of the unit 16 according to FIG. 2. The effective excitation PSF also depends on the light microscope 17 and on the structuring part of the unit 16 according to FIG. 2. In addition, the effective excitation PSF depends on the inherent properties of the fluorophore. According to the present invention, the fluorophore used for labelling a structure of interest in the sample 2 is a photochromic fluorophore which is transferred out of a first photochromic state into a second photochromic state by means of the optical transfer signal 7 according to FIG. 1. As already mentioned there, the optical transfer signal 7 may have the same wavelength as the optical excitation signal 5. Nevertheless, the optical transfer signal 7 has a different function than the optical excitation signal 5. If the photochromic fluorophore in the sample 2 is in its first photochromic state it does not emit any substantial fluorescence light or it does at least not emit that fluorescence light 18 which is registered by the CCD-camera 13 according to FIG. 1. Thus, only those proportions of the photochromic fluorophore result in fluorescence light detected by the CCD-camera 13 which have first been transferred out of its first into its second photochromic state by the optical transfer signal 7 and which have then been excited for fluorescence by the optical excitation signal 5. Thus, in case of a dominant spontaneous off-rate, the effective excitation PSF for the photochromic fluorophore is the product of the PSF of the optical transfer signal 7 within the sample 2 and of the PSF of the optical excitation signal 5 in the sample 2. In this way the spatial resolution in imaging the sample 2 is increased due to the inherent properties of the photochromic fluorophore in a similar way as in 2-photon excitation of a fluorophore in 2-photon fluorescence microscopy. The new method using the photochromic fluorophore, however, avoids a number of strong drawbacks of 2-photon fluorescence microscopy. At first, the yield of fluorescence light from a certain number of molecules of the photochromic fluorophore is much higher in the method according to the present invention than with 2-photon excitation of a fluorophore. At second, the wavelength of the optical excitation signal 5 and the optical transfer signal 7, which may even be identical, are much closer to the wavelength of the fluorescence light 18 in the new method than with 2-photon excitation. Thus, the objective 4 according to FIG. 1 or the light microscope 17 according to FIG. 2 has not to be compensated for chromatic errors due to strongly differing wavelengths. This may be especially interesting in the near UV-range. At third, the light sources suitable for 2-photon excitation of fluorophores suitable for fluorescence microscopy are complicated and expensive due to the short pulses at long wavelengths required for 2-photon excitation. The light source 15 according to FIG. 2 or the lasers 6 and 8 according to FIG. 1 may simply work in the usual wavelength range for 1-photon excitation and may thus be quite low cost.

Figure 3:
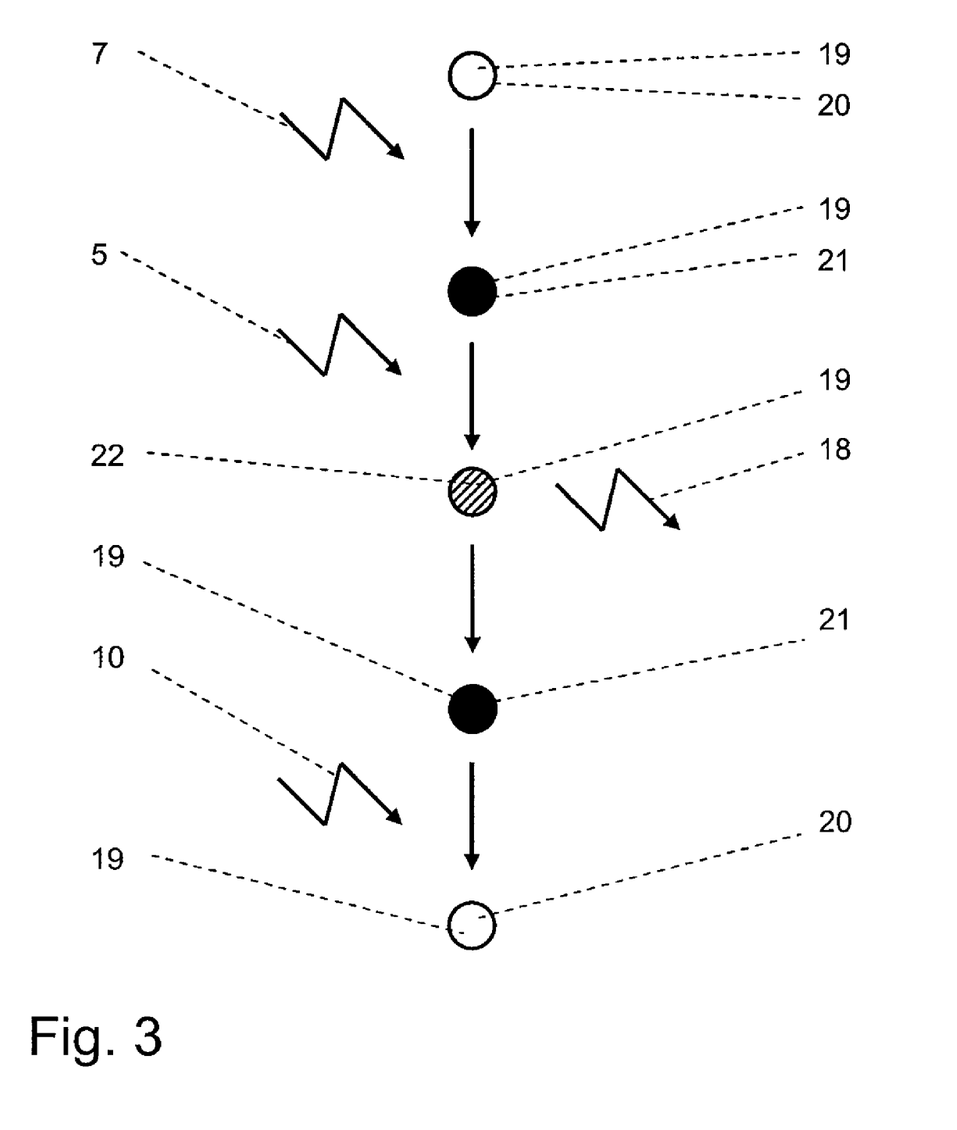
FIG. 3 is a diagram showing the various states through which a fluorophore passes in the new method.

FIG. 3 illustrates a cycle of the states through which a molecule of the photochromic fluorophore 19 passes during the steps of the method of the present invention. At the beginning the fluorophore 19 is in its first photochromic state 20. In this first photochromic state 20 the fluorophore is not excitable for the emission of that fluorescence light 18 which is of interest here. By means of a photon of the optical transfer signal 5 the fluorophore 19 is transferred into its second photochromic state 21. In this second photochromic state 21 the fluorophore 19 is excitable for fluorescence. Thus, the second photochromic state 21 may be called the fluorescent state of the fluorophore 19. In its second photochromic state 21 the fluorophore 19 may absorb a photon of the optical excitation signal 5 to get into an excited second photochromic state 22. This excited second photochromic state 22 has a very short life time as compared to the lifetime of the second photochromic state 21, the excited second state 22 being an energetic sub-state of the second photochromic state 21. Out of its excited second photochromic state 22 the fluorophore 19 returns into its second photochromic state 21 upon spontaneous emission of a photon of fluorescence light 18. This fluorescence light 18 is detected in the new method to image a structure of interest labelled with the fluorophore 19. As soon as the fluorophore 19 is back in its second photochromic state 21 the fluorophore 19 may be again excited for fluorescence by another photon of the excitation signal 5. The number of fluorescence cycles including the absorption of a photon of the optical excitation signal 5 and the emission of a photon of fluorescence light 18 during the life time of the second photochromic state 21 of the fluorophore 19 may be quite high. The life time of the second photochromic state 21 of the fluorophore 19 may be limited by thermal effects, i.e. by a thermal excitation of the fluorophore 19 for returning into its first photochromic state 20. FIG. 3 depicts the additional option that the fluorophore 21 is actively returned out of its second photochromic state 21 into its first photochromic state 20 by means of the optical return signal 10. As already mentioned before, the wavelength of the optical transfer signal 7 and the optical excitation signal 5 or the wavelength of the optical excitation signal 5 and the optical return signal 10, if used, may be identical as the absorption spectra of some photochromic fluorophores 19 comprise overlapping absorption peaks for optical transfer signals and optical excitation signals on the one hand and optical excitation signals and optical return signals on the other hand. Within these overlaps the wavelength of an optical signal serving two purposes may be tuned in such a way that the transition probabilities involved are optimized with regard to a maximum yield of fluorescence light at a maximum spatial limitation of the origin of the fluorescence light 18. As soon as the photochromic fluorophore 19 is back in its first photochromic state 20 it is ready for being transferred again into its second photochromic state 21. The return of the fluorophore 19 into its first photochromic state 20 and the possibility of repeatedly temporally transferring the fluorophore 20 out its first photochromic state 20 into its second photochromic state 21 are preconditions of measuring a sample in closely adjacent points, i.e. of scanning a sample.

Study: Fluorescence Switching Microscopy: A New Principle for High Resolution 3d-Microscopy The inventors denoting the present as Fluorescence Switching Microscopy (FSM) have conducted the following study.

Abstract:

Fluorescence switching microscopy (FSM) enables optical sectioning without requiring confocal optics or 2-photon excitation. We demonstrate that by the use of reversibly switchable fluorophores axial signal discrimination can be readily achieved by the illumination beams only. Hence fast CCD camera detection is enabled with axial discrimination comparable to confocal and 2-photon setups. Together with fluorescent proteins such as DRONPA fast 3d life cell imaging becomes possible. The presented point spread function (PSF) calculations suggest that switching supported fluorescence may perfect other high resolution imaging techniques such as 4Pi, STED and PALM additionally by introducing an axial resolution in the 70 nm range.

Introduction:

Since the development of fluorescence microscopy it has played an ever increasing role in biological research. But it was not until the invention of the confocal microscope in 1957 that a 3-dimensional optical sectioning could be obtained. Before that, fluorescence microscopy was limited to discriminating objects in the lateral direction only.

Confocal microscopy overcomes this limitation by scanning the object by a point of light and using a pinhole in the detection path which leads to a pointlike excitation and detection point spread function (PSF). The effective point-spread function (ePSF) of a confocal microscope is given by the product of the excitation PSF $h_{exc}$ and the detection PSF $h_{det}$, i.e. $h_{eff} = h_{exc} \cdot h_{det}$. The PSFs are given by the square of the electromagnetic fields of excitation and detection, respectively, and can be calculated according to a vectorial theory by Richards and Wolf: $h_{eff} \sim |E_{exc}|^2 \cdot |E_{det}|^2 \otimes p(r)$. Here $p(r)$ denotes the pinhole function, which is 1 for an infinitely small pinhole, i.e. pointlike detection.

The product of the two PSFs leads to a spatial discrimination of the fluorescence signal along the optical (z) axis. The axial FWHM in a confocal microscope typically amounts to 500 nm.

A second possibility to obtain axial discrimination was invented in 1990 by Denk et al. This method is based on 2-photon excitation of the fluorophores in the focus. Only in the focus the light intensity is sufficiently high to allow the 2-photon absorption. The excitation point spread function is squared and thus leads to an axial discrimination of the fluorescence signal. The ePSF of a 2-photon microscope (with CCD-detection) can be described as: $h_{eff} = h_{exc}^2(\underline{x}) \delta(z) \cdot h_{det}$, where the convolution of $h_{exc}^2$ with $\delta(z)$ accounts for the contribution of the scanned xy-plane. The axial FWHM of the 2-photon PSF is approximately comparable to the FWHM of the confocal PSF. Both techniques are successfully used in a wide range of biomedical applications.

The common feature of these two techniques, however, is that their effective point-spread function (ePSF) $h_{eff}(r)$ contains the product of two PSFs of focused beams: In a confocal microscope the localized excitation PSF is multiplied with the localized detection PSF, whereas in the 2-photon case the axial discrimination comes from the squaring of the localized illumination PSF. Here, the axial discrimination is already obtained by the illumination properties, rendering confocal detection obsolete. Therefore in a 2-photon microscope, the fluorescence light can simply be detected by a CCD-camera.

The axial discrimination in confocal microscopy and 2-photon microscopy can be generalized: whenever at least two localized PSFs are multiplied in the imaging process, be it illumination PSF and excitation PSF, or two times the illumination PSF, an axial discrimination and therefore a 3-dimensional resolution can be achieved. If even more PSFs of focusing beams contribute to the effective PSF, the resolution in all directions gets even better, due to the multiplication of the contributing distributions.

Building on this concept, we present a new method called fluorescence switching microscopy (FSM) to achieve 3-dimensional resolution. This method relies on reversibly switchable fluorescent proteins or organic dyes. These proteins have to be optically switched-on before they can be excited and finally fluorescence can be detected. Therefore a switching PSF is multiplied with the excitation PSF and this way 3-dimensional resolution is already obtained by the illumination process. This means that no pinhole is necessary in the detection path, greatly simplifying the setup. Furthermore it is possible to detect the fluorescence light with a high efficiency non-confocally even from both sides of the sample with non-de-scanned detectors, which in principle doubles the fluorescence collection efficiency. Additionally, the setup yields a higher efficiency compared to a 2-photon microscope as there are only 1-photon processes involved.

This new concept circumvents the drawback of the confocal microscope which is rather complex, because a proper alignment is necessary. Furthermore, confocal setups always require a compromise between selecting a small pinhole size for efficient depth discrimination or a large pinhole size for high photon collection efficiency.

In comparison to the 2-photon microscope on the other hand the new concept does not suffer from lower signal compared to 1-photon excitation and does not require an expensive 2-photon laser.

Theory:

The optical transfer function (OTF) of a microscope is given by the fourier transform of the PSF. In case of a widefield microscope the OTF features the so-called "missing cone", where no spatial frequencies along the optical axis are transmitted. This prevents the axial discrimination of laterally extended object structures. In general the missing cone is not present, if the PSF describing the imaging properties contains the product of at least two focused beams of light. This is true in a confocal microscopy, as well as in 2-photon microscopy as described above.

In FSM the missing cone is avoided when a fluorescence switching and excitation beam coincide to generate localized fluorescence signals.

We performed calculations to evaluate the FWHM of the PSF for a FSM with non-confocal detection, i.e. we assumed that the structured switching and excitation beams are scanned across the sample while the fluorescence light is accumulated in the CCD. The effective PSF for non-confocal CCD-detection is given by the product of the switching and excitation PSFs ($h_{act}$ and $h_{exc}$). Scanning both illumination beams across a sample and detecting leads to the effective PSF: $h_{eff} = (h_{act} \cdot h_{exc})(\underline{x}) \delta(z) \cdot h_{det}$. Here the illumination structure may be a single or multiple spots or lines or other preferably focussed structures.

A scanned spot with switching at 405 nm, and excitation at 488 nm and a fluorescence at around 515 nm theoretically features an axial FWHM of 231 nm using a 1.46 NA Oil immersion objective. Note these results are valid in general as long as switching and excitation take place simultaneously with preferably diffraction limited illumination structures.

However, in order to make use of this novel method, a dye has to be found, which fulfills special requirements. First of all the dye needed has to be reversibly switchable for many cycles between two spectroscopically distinguishable states.

In the following we assume that the selected molecule can be reversibly switched between a fluorescent or active or on state and a dark or inactive or off state. If the dye for example is activated by light of a certain wavelength and is excited and deactivated at a second wavelength, then further conditions required for optical sectioning become obvious by watching the rate equation $\dot{n}_{on} = n_{off} k_{on} - n_{on} k_{off}$ for the transitions between the active and inactive state in the equilibrium. Here the concentration of active molecules is $$n_{on} = \frac{k_{on}}{k_{on} + k_{off}} \text{ or } n_{on} \cong \frac{k_{on}}{k_{off}}$$

at a low saturation level which is most desirable. In a simplistic view the switching and excitation beams are considered as being conical with an intensity proportionally to the square of the inverse of the focal distance. The rate constants are then given by $$k_{on} = b \cdot \frac{P_{act}}{z^2} + k_{spon}$$

and $$k_{off} = c \cdot \frac{P_{exc}}{z^2} + k_{spoff},$$

respectively, b and c being constants; P being the powers of the beams of light; and $k_{spon}$ and $k_{spoff}$ being spontaneous transition rates into the on and off state, respectively.

Note that optical sectioning is achieved only in those cases in which the concentration of active molecules is decreasing with the distance from the focal region.

For molecules which are deactivated by the excitation beam we get:

$$n_{on}(z) = \frac{b \cdot \frac{P_{act}}{z^2} + k_{spon}}{c \cdot \frac{P_{exc}}{z^2} + k_{spoff}}$$

Thus, in general at large focal distances the spontaneous rates determine $n_{on}$ whereas in the focus the spontaneous rates are negligible. The latter is the case of the images shown in the Ando 2007 paper, where confocal images are shown which necessarily only show in focus light due to the confocal effect.

Other cases to be considered are:

1. In the case of bi-stable molecules the spontaneous rates are zero and the z-dependence vanishes.
2. If $k_{spon}$ is dominant and the molecules switch to the active state quickly, then more light is collected from out of focus regions in dense samples. May be this is why Ando et al. speculate that these molecules might be useful for wide field imaging when the laser lines are focused by separate objectives each and the above formula do not necessarily apply. Unfortunately, Ando et al. do not describe any further details here.
3. The most desirable case is in which the molecules exhibit a fast (roughly in the order of the pixel and the line dwell time) spontaneous back transition into the dark state. Then the concentration of active molecules essentially decreases with the square of the focal distance comparable to the confocal or 2-photon excitation case. In this case the lasers can be focused by the same objectives, which simplifies the setup.
4. If $k_{spon}$ is small enough, then a less strong optical sectioning capability may be achieved by using an essentially line shaped excitation beam. Out of focus light is then suppressed essentially proportional to the focal distance z as in a confocal line scanning device. Note this case may also apply when switching is fast and the switch off rate is slow compared to the scanning rate of the focused beam.
5. Still another possibility is to include an extra switch off step in the image acquisition sequence.

Luckily an increasing number of switch-able fluorescent proteins such as DRONPA and its mutants and switchable organic dyes such as SpaRhodamines and others became available recently (Stiel et al, Ando et al., Fölling et al.). Ando et al. show cells labeled with switch-able dyes which display fluorescence only, if both switching and excitation light are applied simultaneously. Ando et al. used a dye which quickly returned into its active state. So they had to use a confocal microscope to suppress the out of focus light. Ando et al. actually suggest the use of switch-able dyes for wide field detection when two different objectives are used for the two lasers. In our case both lasers can use the same beam paths, which leads to a much simpler optical setup.

Still another class of dyes such as the ASCP type are switched on at the excitation wavelength and are switched off in the near UV range. Of course, the rate equations must be modified accordingly, here.

In this work we are using an extremely fast-switching mutant of DRONPA, i.e. Dr31, which we found to match our requirements sufficiently to prove the general principle. Dr31 can be activated in the UV-range (at around 400 nm), or alternatively with two-photon activation at around 800 nm. The excitation takes place at 488 nm, and the fluorescence is 515 nm. The readout process at 488 nm simultaneously switches the DRONPA-mutant into its off-state.

Experiments:

In order to demonstrate the 3-D capability of our approach, we performed measurements on a Dr31-layer in a non-confocal optical setup. For switching we used 405 nm and for excitation we used 488 nm. As a negative control, we performed experiments on a GFP-layer, which was excited also at 488 nm. As expected the control experiment shows no axial discrimination, whereas the measurement on the Dr31-layer features an optical sectioning property as expected.

Figure 4:
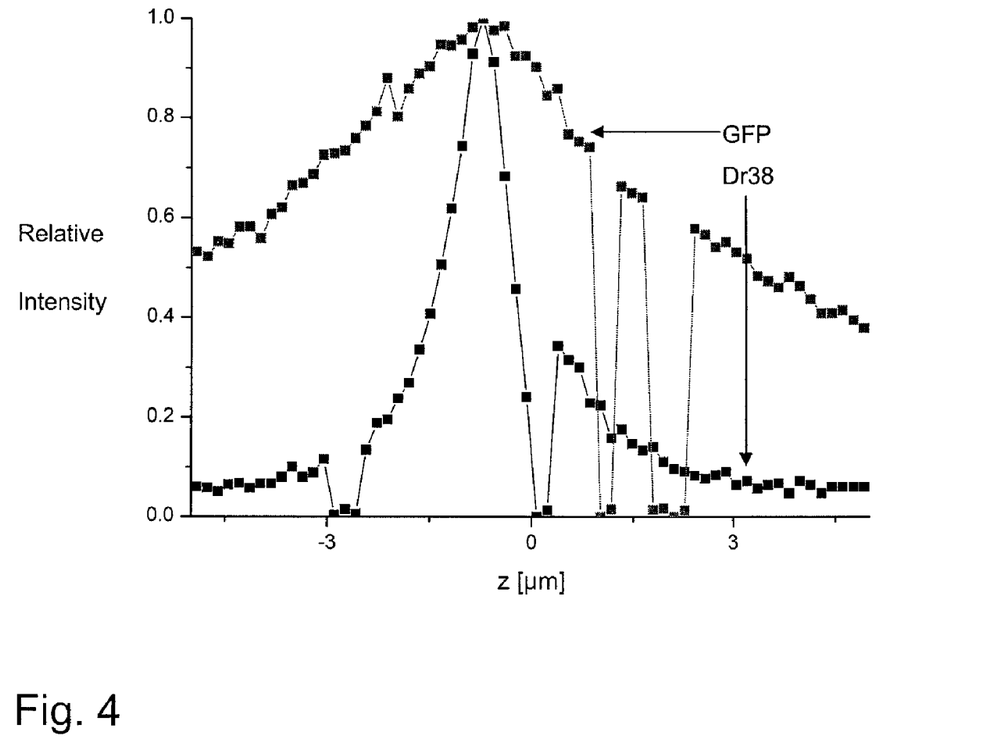
FIG. 4 shows an intensity profile along the optical axis of a thin layer of fluorescence dyes detected by a non-confocal large area detector.

FIG. 4 shows intensity profiles along the optical axis of the thin layer of fluorescence dyes detected by a non confocal large area detector. The intensity profiles indicate that the switching of Dronpa delivers depth discrimination even in laterally extended structures which is not present in the control experiment using regular GFP fluorescent dyes. Note that the slow drop the intensity in the GFP case is due to the finite beam diameters in the microscope setup.

CONCLUSION AND DISCUSSION

In this study we presented a new method for 3d-microscopy, based on simultaneous switching and excitation of a switchable dye. The presented FSM-PSF calculations show that whenever the effective PSF is the product of two or more PSFs of focused beams simultaneously, then a real axial discrimination property can achieved as in confocal or 2-photon microscopy.

The presented data is just an example of the new general method enabled by the recent advent of photo-stable, fast-switching fluorescent markers.

The general statements of the described imaging properties hold true for any other scenarios involving the product of 2 or more PSFs using different switching schemes such as photo induced color changes etc.

We demonstrated the feasibility of this new method on a layer of dr31, a fast switching fluorescent protein. We showed that neither a confocal pinhole, nor a 2-photon laser is necessary and 3-dimensional resolution is achieved solely by the use of switchable dyes.

The use of fluorescent proteins offers the possibility for fast 3D in-vivo imaging, especially when the sample is illuminated by multiple spots or lines or other preferably diffraction limited structures. These may be generated by a variety of methods using devices such as micro lens arrays, SLMs, LCD or DMD projectors, LED arrays, holographic pattern generators etc.

With 1-photon activation and excitation multi spot or even line illumination pattern are applicable which for power reasons would not be possible with ultra fast lasers.

In order to avoid increased photo-toxicity by activation of dyes such as DRONPA with near UV light, of course activation can also be accomplished by 2-photon absorption at 800 nm simultaneously with a 488 nm excitation or other wavelengths from new dyes which may become available.

Note that bleaching processes out of the S1 state are expected to take place only in the very focus when fluorescence after photo-activation is used in very much the same way as in the 2-photon excitation case.

Of course the benefit of the additional switching step is not limited to regular 3d microscopy only.

The method of using photo switch-able dye molecules offers a new quality in high resolution 3d imaging in 4Pi with respect to probe size, side-lobe reduction and imaging speed. 4Pi microscopy is boosted by the additional kick of switching which reduces the effective detection volume to less than 1 atto liter which will be especially helpful in 3-dimensionally dens structures.

It should also be noted that FSM may be advantageously used in many other microscopy techniques such as high throughput applications where it also suppresses effectively light generated not in the focus.

We also expect in non microscopic applications such as optical tomography significant advantages due to the suppression of out of focus light.

Since techniques such as STED, PALM etc. can only improve the pre-existing diffraction limited resolution by a certain factor, 4Pi with switch-able dyes may eventually be the best starting point for these methods of resolution enhancements beyond the diffraction limit.

We expect that also PALM techniques (Betzig) will be blessed with an additional appreciable axial resolution in the 70 nm range.

A diffraction limited far-field optical resolution below 70 nm based on pure physical instrument properties is predicted.

Many variations and modifications may be made to the preferred embodiments of the invention without departing substantially from the spirit and principles of the invention. All such modifications and variations are intended to be included herein within the scope of the present invention, as defined by the following claims.

REFERENCES

Stiel, A. C., S. Trowitzsch, G. Weber, M. Andresen, C. Eggeling, S. W. Hell, S. Jakobs, and M. C. Wahl, "1.8 A° bright-state structure of the reversibly switchable fluorescent protein Dronpa guides the generation of fast switching variants". Biochem. J. (2007) 402:35-42

R. Ando, C. Flors, H. Mizuno, J. Hofkens and A. Miyawaki, "Highlighted Generation of Fluorescence Signals Using Simultaneous Two-Color Irradiation on Dronpa Mutants", Biophysical Journal: Biophysical Letters (2007), L97ff, DOI: 10.1529/biophysj.107.105882

Jonas Fölling, Vladimir Belov, D. Riedel, Andreas Schönle, Alexander Egner, Christian Eggeling, Mariano Bossi, and Stefan W. Hell, "Fluorescence Nanoscopy with Optical Sectioning by Two-Photon Induced Molecular Switching using Continuous-Wave Lasers", ChemPhysChem (2008), 9, 321-326, DOI: 10.1002/cphc.200700655

Betzig, E., G. Patterson, R. Sougrat, O. Lindwasser, S. Olenych, J. Bonifacino, M. Davidson, J. Lippincott-Schwartz, and H. Hess, "Imaging intracellular fluorescent proteins at nanometer resolution.", Science (2006), 313:1642-1645

LIST OF REFERENCE NUMERALS 1 fluorescence microscope
2 sample
3 sample carrier
4 objective
5 optical excitation signal
6 excitation laser
7 optical transfer signal
8 transfer laser
9 return laser
10 return signal
11 dichroitic mirror
12 XY-scanner
13 CCD-camera
14 dichroitic mirror
15 light source
16 structuring/scanning and detection unit
17 light microscope
18 fluorescence light
19 fluorophore
20 first photochromic state
21 second photochromic state
22 excited second photochromic state

The invention claimed is:

1. A method of imaging a structure in a sample with three-dimensional spatial resolution, the method comprising the steps of:

selecting a fluorophore from a group of photochromic fluorophores which are repeatedly temporarily transferable by means of an optical transfer signal out of a first photochromic state into a second photochromic state having fluorescence properties specific to the second photochromic state, and which display a return rate out of the second photochromic state into the first photochromic state;

labelling the structure with the fluorophore;

via a common objective, subjecting the sample in a spatially limited transfer-volume to the optical transfer signal transferring a portion of the fluorophore located in the transfer-volume into its second photochromic state;

via the common objective, subjecting the sample in a spatially limited excitation-volume to an optical excitation signal exciting a portion of the fluorophore located in the excitation-volume and being in its second photochromic state for fluorescence, the transfer-volume and the excitation-volume having a common centre of maximum intensity of the transfer signal and of the excitation signal;

wherein, at least in the direction of the optical axis of the common objective, a decrease of intensity of the transfer signal with the distance to the common centre of maximum intensity is substantially stronger than any decrease of the effective return rate of the fluorophore;

detecting fluorescence light emitted by the excited fluorophore in its second photochromic state located in and about the common centre of maximum intensity of the transfer signal and the excitation signal;

shifting the common centre of maximum intensity of the transfer signal and the excitation signal with regard to the sample; and repeating the preceding steps of subjecting and detecting for the shifted common centre of maximum intensity of the transfer signal and the excitation signal.

2. The method of claim 1, wherein the return rate is spontaneous.

3. The method of claim 2, wherein the fluorophore is selected from a group of fluorophores which display a substantial spontaneous return rate at ambient temperature of the sample.

4. The method of claim 1, wherein the return rate is inducible by means of a physical return signal.

5. The method of claim 4, wherein the fluorophore is selected from a group of fluorophores which display a substantial return rate inducible by means of an optical return signal.

6. The method of claim 4, wherein the return signal is a pulsed signal completely returning the fluorophore into the first photochromic state prior to the steps of subjecting the sample to the transfer signal and the excitation signal and of detecting fluorescence light.

7. The method of claim 1, wherein the group of photochromic fluorophores includes photochromic fluorophores which are at least fluorescent in their second photochromic state, and which are transferred between their first photochromic states and second photochromic states by a process selected from a group of processes including:

cis-/trans-isomerisation,
proton transfer,
atom group transfer,
electron transfer,
ring-opening/closing, and
dimerisation.

8. The method of claim 5, wherein the sample is subjected to the return signal via the common objective, wherein the intensity of the return signal has no zero point at the common centre of maximum intensity.

9. The method of claim 5, wherein the sample is subjected to the return signal via the common objective, wherein the intensity of the return signal has no minimum at the common centre of maximum intensity.

10. The method of claim 5, wherein the sample is subjected to the return signal via the common objective, wherein the intensity of the return signal has a maximum at the common centre of maximum intensity.

11. The method of claim 5, wherein the sample is subjected to a uniform intensity distribution of the return signal about the common centre of maximum intensity.

12. The method of claim 1, wherein the excitation-volume is defined by a local constructive interference of a plurality of different parts of the excitation signal.

13. The method of claim 12, wherein the excitation signal and the transfer signal are both spilt up into two parts which are superimposed in the transfer-volume and the excitation-volume out of opposite directions through two common objectives arranged on opposite sides of the sample, the beam paths of the different parts of both the excitation signal and the transfer signal differing from each other in lengths by less than the coherence lengths of the excitation signal and the transfer signal.

14. The method of claim 1, wherein the transfer-volume is defined by a local constructive interference of a plurality of different parts of the transfer signal.

15. The method of claim 1, wherein the fluorescence light is detected in a spatially limited detection-area having a centre which is confocally arranged with regard to the common centre of maximum intensity of the transfer signal and the excitation signal.

16. The method of claim 1, wherein the sample is three-dimensionally scanned with the common centre of maximum intensity of the transfer signal and the excitation signal.

17. The method of claim 1, wherein the transfer signal and the excitation signal have a same width at half maximum about the common centre of maximum intensity of the transfer signal and the excitation signal.

18. The method of claim 1, wherein all optical signals to which the sample is subjected are continuous wave signals.

19. The method of claim 1, wherein the transfer signal and the excitation signal are identical.

20. A method of imaging a structure in a sample with three-dimensional spatial resolution, the method comprising the steps of:

selecting a fluorophore from a group of photochromic fluorophores
which are repeatedly temporarily transferred out of a first photochromic state into a second photochromic state by means of an optical transfer signal by a process selected from a group of processes including:
cis-/trans-isomerisation,
proton transfer,
atom group transfer,
electron transfer,
ring-opening/closing, and
dimerisation,
which are at least fluorescent in their second photochromic state and have fluorescence properties specific to the second photochromic state, and
which display a return rate out of the second photochromic state into the first photochromic state, the return rate being inducible by means of a physical return signal;
labelling the structure with the fluorophore;
via a common objective, subjecting the sample in a spatially limited transfer-volume to the optical transfer signal transferring a portion of the fluorophore located in the transfer-volume into its second photochromic state;
via the common objective, subjecting the sample in a spatially limited excitation-volume to an optical excitation signal exciting a portion of the fluorophore located in the excitation-volume and being in its second photochromic state for fluorescence, the transfer-volume and the excitation-volume having a common centre of maximum intensity of the transfer signal and of the excitation signal;
via the common objective, subjecting the sample to the return signal, the intensity of the return signal having no minimum at the common centre of maximum intensity of the transfer signal and the excitation signal;
wherein, at least in the direction of the optical axis of the common objective, a decrease of intensity of the transfer signal with the distance to the common centre of maximum intensity is substantially stronger than any decrease of the effective return rate of the fluorophore;
detecting fluorescence light emitted by the excited fluorophore in its second photochromic state located in and about the common centre of maximum intensity of the transfer signal and the excitation signal;
shifting the common centre of maximum intensity of the transfer signal and the excitation signal with regard to the sample; and
repeating the preceding steps of subjecting and detecting for the shifted common centre of maximum intensity of the transfer signal and the excitation signal for three-dimensionally scanning the sample with the common centre of maximum intensity of the transfer signal and the excitation signal.

* * * * *